United States Patent [19]

Thompson et al.

[11] Patent Number: 4,943,535
[45] Date of Patent: Jul. 24, 1990

[54] ANTI-LIFT FERMENTER

[75] Inventors: Philip W. Thompson; Lesley A. Wood, both of Slough, Great Britain

[73] Assignee: Celltech Limited, Slough, England

[21] Appl. No.: 47,917

[22] PCT Filed: Jun. 20, 1986

[86] PCT No.: PCT/GB86/00359
§ 371 Date: Apr. 6, 1987
§ 102(e) Date: Apr. 6, 1987

[87] PCT Pub. No.: WO86/07605
PCT Pub. Date: Dec. 31, 1986

[30] Foreign Application Priority Data

Jun. 20, 1985 [GB] United Kingdom ............ 8515629

[51] Int. Cl.$^5$ .............................................. C12M 1/12
[52] U.S. Cl. ...................................... 435/311; 435/286; 435/314
[58] Field of Search ...................... 435/311, 314, 286

[56] References Cited

U.S. PATENT DOCUMENTS 4,178,209 12/1979 Tolbert et al. .
4,183,787 1/1980 Roesler et al. .................. 435/43
4,276,384 6/1981 Mueller ........................... 435/311

FOREIGN PATENT DOCUMENTS 0007133 1/1980 European Pat. Off. .
52252 5/1982 European Pat. Off. ............ 435/311
0073079 3/1983 European Pat. Off. .
0113328 12/1983 European Pat. Off. .
1238401 7/1971 United Kingdom .
2163453 2/1986 United Kingdom .

Primary Examiner—Martin P. Schwadron
Assistant Examiner—Allen J. Flanigan
Attorney, Agent, or Firm—Spencer & Frank

[57] ABSTRACT

A continuous fermenter vessel such as an air-lift, fermenter for receiving and cultivating a suspension culture of cells. The vessel contains a mechanism for agitating the suspension culture received in the vessel and causing a gross flow movement of the suspension culture. The vessel includes an inlet for continuously supplying culture medium to the vessel and an outlet for removing the culture supernatant. A filter material is disposed inside the vessel so that the gross flow movement of the suspension culture substantially prevents clogging of the filter material by cells and/or cell debris.

6 Claims, 1 Drawing Sheet

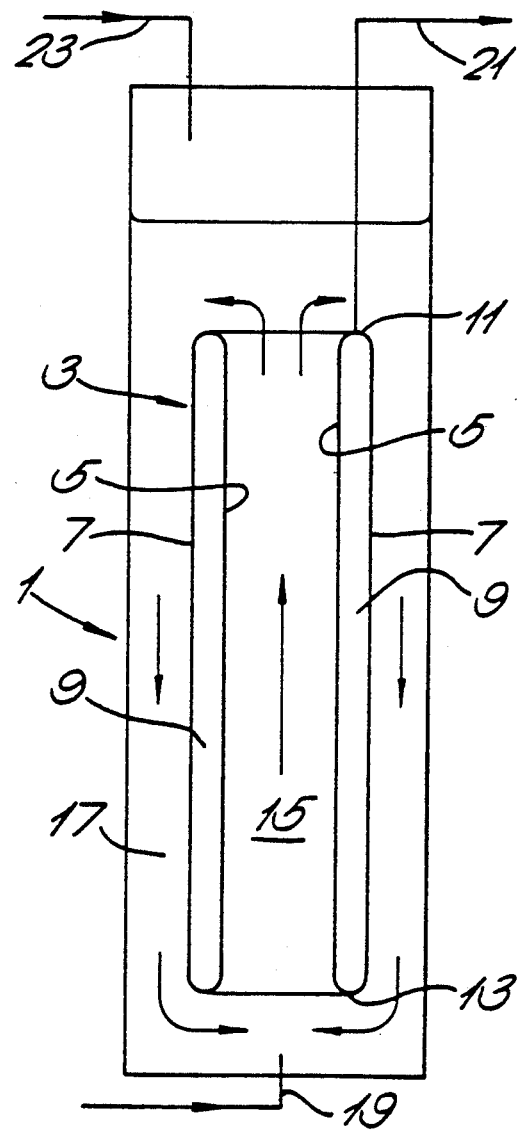

ANTI-LIFT FERMENTER

BACKGROUND OF THE INVENTION

1. Field of the Invention

This invention relates to a continuous fermenter vessel for receiving an agitated suspension culture of cells.

2. Description of the Prior Art

Recent advances in the commercialization of products produced by the in vitro fermentation of cells have led to a growing interest in the design of improved fermenter vessels and fermentation processes.

Fermentation is usually carried out either in a batch process or in a continuous process. Continuous processes are advantageous since they enhance the productivity of a given fermenter and reduce the downtime necessary for cleaning and sterilization which is normally required in a batch fermenter.

In known continuous fermenter vessels, a suspension of cells in an appropriate culture medium is agitated and maintained at a suitable temperature for fermentation. Suspension culture is continuously withdrawn from the fermenter, balanced by a continuous supply of fresh culture medium. A significant disadvantage of such fermenters is the continual loss of cells caused by the removal of culture. Fermenters are known in which the removed suspension culture is passed through a continuous centrifugal separation device which separates cells from the culture supernatant. The cells are then fed back into the suspension culture.

In another known fermenter, a rotating basket of a filter material is provided, partially submerged in the culture, such that the inside of the basket is separated from the suspension culture by the filter. Culture supernatant passes through the filter and may be withdrawn continuously, whilst cells remain in the suspension culture. The rotation of the basket in the suspension culture reduces clogging of the filter material.

These known devices for providing cell feedback in continuous suspension cultures are complicated mechanically, require energy for their operation and may cause detrimental effects, such as cell rupture, upon the suspension culture. These features combine to reduce the economic viability of fermentation processes based on such fermenters.

SUMMARY OF THE INVENTION

The object of the present invention is to provide a continuous fermenter vessel which substantially overcomes these disadvantages.

According to the present invention there is provided a continuous fermenter vessel for receiving a suspension culture of cells, the vessel comprising; means, in use, for agitating a suspension culture received in the vessel and causing a gross flow movement of the suspension culture, an inlet for continuously supplying culture medium to the vessel, an outlet for removing culture supernatant, and a filter material between the outlet and the vessel to prevent removal of cells from the suspension culture wherein the filter material is located such that, in use, the gross flow movement of the suspension culture substantially prevents clogging of the filter material by cells and/or cell debris.

The fermenter vessel of the invention requires no moving parts in order to achieve separation of the culture supernatant from the suspension and therefore provides an advantageous saving in costs. The filter material has a pore size which depends upon the diameter of the cells to be cultured. For animal cells the filter material may have a pore size of from 1 to 10 $\mu$m, 1 to 5 $\mu$m, and most preferably 3 to 5 $\mu$m. The filter material may be a ceramics material, sintered stainless steel or a stainless steel mesh.

Gross flow movement of the culture supernatant may be produced using a pump or impeller. However such devices add to the cost and complexity of the fermenter. In a preferred form of the invention the fermenter is a so called "air-lift" fermenter in which a gas such as air is injected into an upwardly extending part of the fermenter known in the art as a "riser". The riser communicates at top and bottom with the top and bottom respectively of a further upwardly extending part of the fermenter known in the art as a "downcomer". A known configuration of an air-lift fermenter comprises a central divider in the fermenter vessel separating the vessel into two parts (riser and downcomer). An alternative configuration of air-lift fermenter comprises a draught tube substantially concentric with a cylindrical fermenter vessel, dividing the fermenter into a riser (within the draught tube) and a downcomer (in the annular space between the draught tube and the inside of the fermenter vessel). (The riser could equally be the annular space between the draught tube and the inside of the fermenter vessel, and the downcomer could be within the draught tube). The injection of a gas, such as air, into the lower part of the riser causes a reduction in the bulk density within the riser resulting in an upward flow of liquid in the riser, thus displacing the contents of the downcomer which circulate back into the bottom of the riser. In this way a recycling fluid flow is caused, mixing the culture and maintaining the cell suspension. The advantages of such a fermenter are that no moving parts are necessary and oxygenation of the culture occurs. Typically the cross-sectional area of the riser is substantially the same as the cross-sectional area of the downcomer.

In a preferred aspect of the invention, the continuous fermenter vessel is an air-lift fermenter and the outlet comprises a conduit formed in a divider between a downcomer and a riser, the conduit communicating with the fermenter vessel via a filter material forming at least a part of the divider. In this way, suspension culture either flowing up the riser or down the downcomer flows tangentially across the filter material substantially preventing clogging of the filter with cells from the culture. Culture supernatant may be drawn into the conduit within the divider and removed from the conduit via an outlet port. Preferably the divider comprises a double-walled draught tube defining, between the double-walls, a conduit space communicating in use with the suspension culture through at least a portion of the draught tube comprising a filter material. The draught tube may be formed such that the inside of the draught tube (i.e. in the riser) is formed of a continuous material and the outside of the draught tube (i.e. in the downcomer) is formed of a filter material such as sintered or mesh stainless steel.

The circulation flow rate may be increased by increasing the gas flow rate and hence the circulation velocity. To prevent over oxygenation of the fermenter contents, the air may be mixed with an inert gas, such as nitrogen, in order to maintain a sufficiently high overall gas flow rate while limiting the oxygen transfer rate. An increase in the aspect ratio (height:diameter) of the fermenter will cause an increase in the circulation distance and hence for a specific circulation flow rate (which is generated by specific air flow rate) the circulation velocity will be increased.

The fermenter may be used for the culture of any cells capable of in vitro growth in suspension liquid culture (including microcarrier culture), but is especially useful for the culture of animal cells such as, for example, hybridoma cell lines.

BRIEF DESCRIPTION OF THE DRAWINGS

The invention is now illustrated by the following description with reference to the accompanying drawing, which is a schematic axial cross-section of an air-lift fermenter of the invention including a double-walled draught tube concentric with a fermenter vessel.

DESCRIPTION OF THE PREFERRED EMBODIMENTS

Referring to FIG. 1 an air-lift fermenter comprises a cylindrical outer vessel shown generally at 1. A draught tube shown generally at 3, is located concentrically within the outer vessel 1. The draught tube consists of a double-walled cylinder comprising inner and outer cylindrical walls, 5, 7 respectively, sealed at each end by annular caps 11 and 13 forming an annular conduit 9. At least a portion of the inner and/or outer walls 5 and 7 of the cylindrical draught tube 3 comprises a filter material capable of allowing passage of culture supernatant but preventing the passage of cells. A suitable filter material is sintered stainless steel or a stainless steel mesh. The pore size of the filter depends upon the cells to be cultured. In the case of animal cells a pore size in the range 1 to 10 $\mu$m is effective. The inside of the draught tube 3, in use, acts as the riser 15 and the annular space between the outer wall 7 of the draught tube 3 and the inner wall of the outer vessel 1 acts as the downcomer 17.

The base of the outer vessel 1 carries an air inlet 19 directly below and approximately central with respect to the riser 15. The top of the conduit 9 is provided with an outlet 21 for withdrawing culture supernatant. The fermenter is provided with an inlet 23 for supplying culture medium to the fermenter. Thermostatically controlled heating means may be provided either in or around the outer vessel 1. The outer vessel 1 may be double-walled to provide a jacket, for example filled with water.

In use, a suspension culture of cells, suitably animal cells, is introduced into the fermenter such that the top of the draught tube 3 is covered by a depth of the suspension culture corresponding to from 0.25 to 1.0 times the diameter of the outer vessel 1. The suspension culture is maintained in a flow condition by forcing air through air inlet 19. The air rises within the riser 15 reducing the bulk density of the liquid suspension in the riser 15 and causing a gross flow movement of liquid in the direction indicated by the arrows in FIG. 1. At the top of the riser 15, air within the suspension culture is disengaged. A continuous supply of culture medium is provided through inlet 23. The culture medium includes nutrients and other factors necessary for the efficient culture of the cells. Culture supernatant is continuously drawn through the filter material forming at least a part of the double-walls 5 and 7 of the draught tube 3. Culture supernatant drawn into the conduit 9 is then withdrawn from the fermenter through outlet 21. The filter material may form a part or all of either or both of the double-walls 5 and 7 of the draught tube 3.

Experiments have revealed that for a range of fermenter sizes of 100 liters to 1,000 liters with aspect ratios (height:diameter) of from 8 to 12 and using an air flow rate of 0.1 vvm, the circulation velocity in both the riser and downcomer ranges from 0.15 ms$^{-1}$ to 0.25 ms$^{-1}$. The geometry of the riser and downcomer and the air flow rate may be adjusted in order to achieve a sufficient circulation velocity to prevent clogging of the filter. The pressure of the air in the headspace may be increased to achieve a greater flow through the filter if clogging does occur.

A continuous culture was run using a 301 continuous air-lift fermenter provided with a nominal 10 $\mu$m pore size stainless steel mesh filter. The fermenter was substantially as shown in the accompanying FIGURE wherein the outer wall 7 comprises a nominal 10 $\mu$m stainless steel mesh ("Hollander Twill Weave"—Simon Cadish & Sons, U.K.) on a much larger hole size backing cylinder. The inner wall 5 comprises a continuous stainless steel cylinder. The draught tube is sealed such that any liquid pumped from the vessel must have entered the space between the inner 5 and outer 7 walls through the filter material.

A hybridoma cell-line was cultured in the vessel using a culture medium comprising DMEM, 3.7 g/l NaHCO$_3$ buffer and 5% foetal calf serum, at a dilution rate of approximately 0.03 hr$^{-1}$. The viable cells in the culture and withdrawn from within the draught tube were counted. This indicated that only about 5% of the total viable cells in the culture were passing through the filter.

It will be understood that the present invention has been described above purely by way of example, and modifications of detail can be made within the scope and spirit of the invention.

We claim:

1. A continuous air-lift fermenter vessel for receiving a suspension culture of cells, the vessel comprising:
air-lift means, in use for agitating a suspension culture received in the vessel and causing a gross flow movement of the suspension culture, an inlet for continuously supplying culture medium to the vessel, an outlet for removing culture supernatant, and a filter material between the outlet and the vessel to prevent removal of cells from the suspension culture wherein the filter material is located such that in use, the gross flow movement of the suspension culture inhibits clogging of the filter material by cells and/or cell debris, said the outlet comprising a conduit formed in a divider between a downcomer and a riser, the conduit communicating with the fermenter vessel via the filter material forming at least a part of the divider, the divider comprising a double-walled draught tube defining, between the double-walls, a conduit space communicating in use with the suspension culture through at least a portion of the draught tube comprising the filter material.

2. A continuous fermenter vessel according to claim 1 wherein the filter material has a pore size of from 1 to 10 $\mu$m.

3. A continuous fermenter vessel according to claim 1 wherein the inside of the draught tube is formed of an impermeable material and at least a portion of the outside of the draught tube is formed of the filter material.

4. A method for the suspension culture of cells comprising culturing the cells in a continuous fermenter vessel according to claim 1.

5. A method according to claim 4 wherein the cells are hybridoma cells.

6. A continuous air-lift fermenter vessel for receiving a suspension culture of cells, said vessel comprising:

an inlet means for continuously supplying culture medium to said vessel;

a divider comprising a filter material and a double-walled draught tube having two concentric walls and a conduit space therebetween, said conduit space communicating with said vessel via said filter material;

a riser and a downcomer each having an upper and lower part and being separated from each other by said divider;

means for injecting a gas into said lower part of said riser for causing a gross flow movement of suspension culture in said vessel comprising an upward flow of suspension culture in said riser and a downward flow of suspension in said downcomer, said gross flow movement of suspension culture allowing culture supernatant to be drawn into said conduit space and inhibiting clogging of said filter material with cells from said suspension culture; and outlet means for removing culture supernatant from said conduit space.

* * * * *